(12) United States Patent
Simon et al.

(10) Patent No.: US 8,303,593 B2
(45) Date of Patent: Nov. 6, 2012

(54) BONE CUTTING TOOL AND METHOD OF USE

(75) Inventors: Bernd Simon, Kiel (DE); Stefan Volzow, Monckeberg (DE)

(73) Assignee: Stryker Trauma GmbH (DE)

( * ) Notice: Subject to any disclaimer, the term of this patent is extended or adjusted under 35 U.S.C. 154(b) by 948 days.

(21) Appl. No.: 10/757,929

(22) Filed: Jan. 15, 2004

(65) Prior Publication Data

US 2004/0167527 A1    Aug. 26, 2004

(30) Foreign Application Priority Data

Jan. 23, 2003    (DE) .............................. 203 00 988 U

(51) Int. Cl.
*A61B 17/16*    (2006.01)
*A61B 17/32*    (2006.01)

(52) U.S. Cl. .............................. 606/80; 606/79; 606/180

(58) Field of Classification Search .................... 606/79, 606/80, 83–85, 184, 167, 170–171, 178–179; 30/352; 604/506, 267, 523; 452/69
See application file for complete search history.

(56) References Cited

U.S. PATENT DOCUMENTS

| | | | | | |
|---|---|---|---|---|---|
| 854,956 | A | * | 5/1907 | Martin | 606/80 |
| 958,854 | A | * | 5/1910 | Bunn | 604/267 |
| 3,216,288 | A | * | 11/1965 | Gardner | 408/202 |
| 4,710,075 | A | * | 12/1987 | Davison | 408/202 |
| 4,798,213 | A | * | 1/1989 | Doppelt | 600/567 |
| 5,171,248 | A | * | 12/1992 | Ellis | 606/102 |
| 5,374,270 | A | * | 12/1994 | McGuire et al. | 606/80 |
| 5,423,823 | A | * | 6/1995 | Schmieding | 606/80 |
| 5,476,467 | A | | 12/1995 | Benoist | |
| 5,624,447 | A | | 4/1997 | Myers | |
| 5,865,834 | A | * | 2/1999 | McGuire | 606/80 |
| 5,928,238 | A | * | 7/1999 | Scarborough et al. | 606/79 |
| 6,200,319 | B1 | | 3/2001 | Storer et al. | |
| 6,216,288 | B1 | * | 4/2001 | Bernau | 4/694 |
| 6,264,661 | B1 | * | 7/2001 | Jerger et al. | 606/100 |
| 6,309,396 | B1 | | 10/2001 | Ritland | |
| 6,514,258 | B1 | * | 2/2003 | Brown et al. | 606/80 |
| 6,592,588 | B1 | * | 7/2003 | Bobic et al. | 606/79 |
| 6,695,551 | B2 | * | 2/2004 | Silver | 408/1 R |
| 6,942,669 | B2 | * | 9/2005 | Kurc | 606/80 |
| 8,197,481 | B2 | * | 6/2012 | Zwirnmann | 606/80 |
| 2003/0097133 | A1 | * | 5/2003 | Green et al. | 606/80 |
| 2004/0052595 | A1 | * | 3/2004 | Dembicks et al. | 408/226 |

FOREIGN PATENT DOCUMENTS

| | | |
|---|---|---|
| DE | 1 752 125 | 9/1971 |
| DE | 36 09 122 C1 | 8/1987 |
| DE | 38 00 482 A1 | 7/1989 |
| EP | 0 861 635 A2 | 9/1998 |
| WO | WO-00/42925 | 7/2000 |
| WO | WO-00/45714 | 8/2000 |

* cited by examiner

*Primary Examiner* — Thomas Barrett
*Assistant Examiner* — Michael T Schaper
(74) *Attorney, Agent, or Firm* — Lerner, David, Littenberg, Krumholz & Mentlik, LLP

(57) ABSTRACT

A boring tool for a bone, particularly the proximal femur, which has an elongate shank having a cutting portion at the front end, and a portion to mount a rotary driving device at the rear end of the shank. The tool has an axial through bore for receiving a guide wire, wherein the shank, in a rear portion, has at least one radial aperture which is open to the axial bore.

17 Claims, 1 Drawing Sheet

BONE CUTTING TOOL AND METHOD OF USE

BACKGROUND OF THE INVENTION

The invention relates to a boring tool for a bone, particularly the proximal femur. More particularly, the invention relates to a tool for forming a bore in the head of the femur for receiving a femoral neck screw.

It is known to use femoral neck pins, particularly femoral neck screws, for the repair of femoral fractures, particularly that of the proximal femur. They are introduced in combination with either a so-called Pohl butt or side plate or a locking nail. In the former case, a butt plate or side plate which is extramedullarily fixed to the bone for example to the outer bone surface, contains a sleeve through which the femoral neck screw is passed. When a locking nail is used, in the latter case, the locking nail has an oblique bore for receiving the femoral neck screw.

To securely anchor the femoral neck screw in the bone, the bone is commonly bored open up to the core thread diameter before the femoral neck screw is threaded in.

Before such a boring procedure is performed, it is necessary first to determine the boring axis and, thus, the position of the femoral neck screw in the bone by X-ray control. This is commonly accomplished with a Kirschner threaded wire. After the correct position is determined the Kirschner threaded wire will be left in the bone and serves as a guide for the boring tool and also subsequently in threading the femoral neck screw. For this reason, both the boring tool and femoral neck screw are provided with an axial through bore, i.e. cannulation.

The boring tool, such as a drill or reamer, has a suitable boring portion at the front end of its elongate shank and a portion at the rear end for connection to a rotary drive tool such as a power drill. The tool can be made in two pieces with a locking portion on one of the pieces to operatively connect the front and rear portions.

Under certain conditions, the comparatively thin Kirschner threaded wire can buckle or warp while being introduced in the femoral neck. Therefore, it is indispensable to monitor the position of the Kirschner threaded wire by X-ray control. This prevents the wire from being unintentionally advanced into the hip joint as the warped portion gets stuck in the bore of the boring tool or femoral neck screw. Consequently, warping or buckling of the wire must be avoided.

SUMMARY OF THE INVENTION

It is one object of the invention to provide a boring tool for a bone, particularly the proximal femur, by which the operator can appreciate even without using X-ray control whether the Kirschner threaded wire has become stuck in the bore while the boring tool is being advanced.

This and other objects of the invention are provided by a boring tool for a bone, particularly for the proximal femur, which comprises an elongate shank, boring portion at the front end, and a drive portion for a rotary driving device at a rear end of the shank. The tool has an axial throughbore for receiving a guide wire. The tool has, adjacent the rear end, at least one window open to the bore. In the preferred embodiment, the boring tool rear end includes two diametrically opposed windows which are open to the axial bore for viewing the guide wire. The windows extend in parallel along the tool and may extend for up to several inches in length or even more.

The preferred tool has a generally cylindrical outer wall surrounding the axial bore. The windows, at the rear drive end of the tool, are in the form of elongated slots cut through the wall. The tool may be made in two sections with a coupling element, such as a quick disconnect element, connecting the portion of the tool which includes a cutter at its leading end and the portion of the tool including the drive element and windows. This allows the use of a plurality of cutters on the same rear portion. One skilled in the art would understand that it is possible for the leading first portion to be a flexible shaft including an axial bore for use with the guide wire. The modular second portion, adjacent the drive end, can then be a solid portion including the window for viewing the guide wire.

The method for using the tool to cut bone tissue includes inserting a guide wire into the tissue and placing a cutting tool having an axial bore for receiving the guide wire over the wire. The cutting tool has a cutting element at a first end and a connecting element for connection to a rotary power source at a second end. The second end includes a window open to the bore for viewing the guide wire.

The surgeon then connects a rotary drive tool to the second end and rotates the tool so that the cutter starts forming a bore or channel in the tissue and the surgeon advances the tool over the guide wire to form a bore in the body tissue. As the tool advances, the surgeon can look through the window in the tool to view the guide wire and ensure that the tool is advancing with respect to the guide wire. Should the guide wire become bound within the tool, such as if it warps or buckles, so that the tool is no longer advancing with respect to the guide wire, the surgeon can see this and then remove the wire from the tool. The surgeon then can reinsert a guide wire through the tool into the tissue, if necessary, using X-rays for proper placement of the guide wire.

In the boring tool of the present invention, the shank has a radial aperture or window, which is connected to the axial bore, in a rear portion thereof. Preferably, two diametrically opposed apertures are provided which are connected to the axial bore.

In a preferred embodiment of the invention, the aperture is of an elongate shape and extends in parallel with the axis of the shank. It is preferred that the aperture be close to the locking portion at the rear of the shank.

The aperture, which is outside the bone and can be viewed during the boring procedure. The window enables the operator to perceive whether a relative movement takes place between the boring tool and Kirschner threaded wire during the advance of the boring tool. If there is no relative movement, the operator will know that the Kirschner threaded wire has become stuck in the bore of the tool and, therefore, needs to be replaced with another. Thus, the at least one opening is an observation window through which the surgeon is informed about the position of the guide wire or pin.

Furthermore, an elongate aperture allows the surgeon to see to which length the Kirschner threaded wire has been driven into the femoral neck because the respective depth of boring tool penetration is commonly determined in the bone. When the position of the Kirschner threaded wire relative to the boring tool changes to a critical extent this requires the boring procedure be terminated and another Kirschner threaded wire to be introduced. While the tool and procedure described herein pertains to forming a bore in the femur the tool and method of use can be applied to any surgical operation which uses a guide wire to guide a cutting tool into tissue.

BRIEF DESCRIPTION OF THE DRAWINGS

The invention will be described in more detail below with reference to an embodiment shown in the drawings.

DETAILED DESCRIPTION

Figure 1:
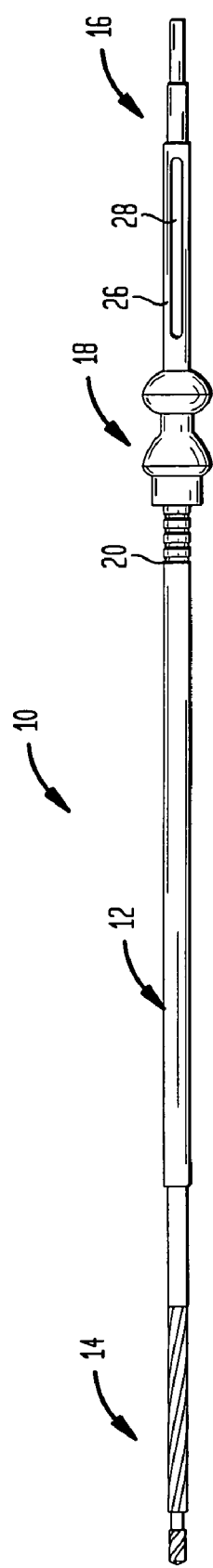
FIG. 1 shows a side view of a boring tool according to the invention.
Figure 2:
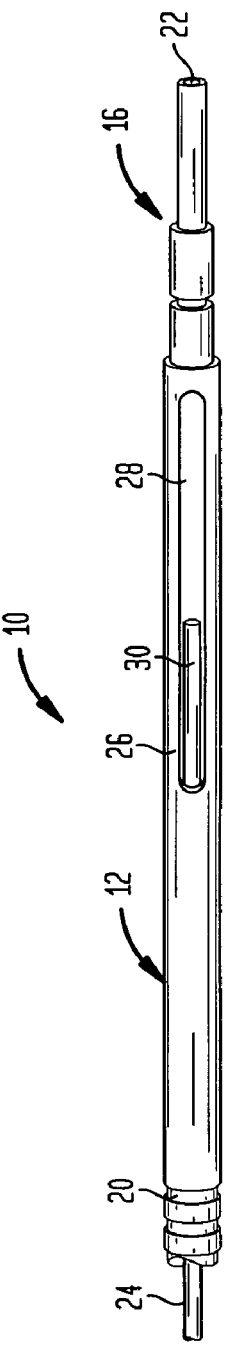
FIG. 2 shows the rear end portion of the boring tool of FIG. 1 in a perspective view.

In FIGS. 1 and 2, a preferred embodiment of boring tool 10 is shown having an elongate shank 12 at the front or leading end which, in the preferred embodiment, has a two-part boring portion 14 which will not be described in detail, other to say that both parts are cannulated to receive a guide wire. Obviously, a single cutter could be utilized at the lead end rather than a two part cutter. Boring tool 10 serves for boring open a femoral neck of a fractured proximal femur so that a standard hip screw can be inserted. The shank 12 is provided with a lock portion 16 at the rear end. A locking portion in the form of a slide 18, which snaps in on shank 12 and is movable thereon but held in a desired position by a spring detent serves for setting the desired bore depth. Individual radial grooves 20 can be seen into which slide 18 may snap and which indicate the boring depth. The adjustable slide 18 is omitted from FIG. 2.

It can be appreciated that preferred tool 10 has an axial through bore 22. Bore 22 serves for receiving a guide wire such as a Kirschner threaded wire 24 a portion of which is shown in FIG. 2. A portion 26 of shank 12, which is close to locking portion 18, has formed therein two axially parallel, elongate slots or windows 28 which, in the preferred embodiment, are diametrically opposed. Slots 28 are in communication with axial bore 22. This allows the surgeon to see the end of the Kirschner threaded wire 24 which is within the axial bore 22 at 30. Therefore, while boring the femur head, the operator can easily view the relative position of the Kirschner threaded wire 24 or free end 30 and find out whether tool 10 is moving relative to the Kirschner threaded wire 24 or is being advanced along with it.

It is understood that several apertures can be provided in lieu of one, which apertures can be disposed to be offset successively, longitudinally or also in a circumferential direction.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for forming a channel in a bone comprising:
a guide wire having a leading and trailing end; and
a rotatable boring tool having proximal end and a distal end, said distal end including a cutting element, and said proximal end adapted to be connected to a power source for rotating said tool to bore into bone, said tool having a wall surrounding an axial bore for slidably receiving said guide wire, said bore being adapted to permit said guide wire to slide axially through said bore when said tool is connected to said power source and while said tool is boring into bone, and said wall adjacent said proximal end having an elongated opening therethrough in communication with said bore, said elongated opening being adapted to permit viewing of axial sliding movement of said guide wire trailing end during rotation of said boring tool while said tool is connected to said power source and said tool is boring into bone; wherein the guide wire is extendable into the bone distally beyond the cutting element of the boring tool and up to a desired depth of the channel to be formed by the cutting element.

2. The system as set forth in claim 1 wherein said opening is in the form of an elongated slot.

3. The system as set forth in claim 2 wherein a second elongated slot is located on an opposite side of said wall from said elongated slot.

4. The system as set forth in claim 1 wherein the elongated opening has a first end and a second end, the first end being spaced from the proximal end of the boring tool, and the second end of the opening being located closer to the cutting element than the first end of the opening.

5. The system as set forth in claim 1 wherein the guide wire is a Kirschner wire.

6. The system as set forth in claim 1 wherein said cutting element has cutting features adapted to cut bone while said tool is rotating and boring into bone, said cutting features extending along a longitudinal axis of said tool.

7. A boring tool for bone, comprising:
a shank having a rotatable cutting tool at a distal end thereof and a drive portion at a proximal end thereof, the shank and cutting tool having a cannulation therethrough, the shank having a pair of diametrically opposed windows therein proximate the proximal end, and the shank having a radially outwardly extending slideable lock portion between the shank distal end and the drive portion, the lock portion being slideable distally and proximally along the shank, the distal end of the shank spaced distally of the lock portion and the drive portion spaced proximally of the lock portion; and
a guide wire slidably received within the cannulation in the shank and cutting tool and having a trailing end viewable through the windows in the shank during rotation of said shank while said shank is connected to a power source and said shank is boring into bone, the guide wire being extendable into a bone distally beyond the cutting tool of the shank and up to a desired depth of a bore to be formed by the cutting tool.

8. The boring tool for bone as set forth in claim 7 wherein said pair of windows extends parallel to the cannulation in the shank.

9. The boring tool for bone as set forth in claim 7 wherein said diametrically opposed windows extend in parallel.

10. The boring tool for bone as set forth in claim 7 wherein each one of the pair of diametrically opposed windows has a first end and a second end, the first end of each window being spaced from the drive portion, and the second end of each window being located closer to the cutting tool than the first end of the respective window.

11. The boring tool for bone as set forth in claim 7 wherein the guide wire is a Kirschner wire.

12. The boring tool for bone as set forth in claim 7 wherein said cutting tool has cutting features adapted to cut bone while said shank is rotating and boring into bone, said cutting features extending along a longitudinal axis of said shank.

13. A system for forming a channel in a bone comprising:
a guide wire having a leading and trailing end; and
an elongate, rotatable boring tool extending along a longitudinal axis, said tool having a boring portion and a drive portion, said boring portion including a cutting element having cutting features adapted to cut bone while said tool is rotating and boring into bone, said cutting features extending along said longitudinal axis, said drive portion disposed proximally of said boring portion along said longitudinal axis of said tool, said drive portion adapted to be connected to a power source for rotating said tool to bore into bone, said tool having a wall surrounding an axial bore for slidably receiving said guide wire, said bore being adapted to permit said guide wire to slide axially through said bore when said tool is connected to said power source and while said tool is boring into bone, and said wall in said drive portion having an elongated opening therethrough in communication with said bore, said elongated opening being adapted to permit viewing of axial sliding movement of said guide wire trailing end during rotation of said boring tool while said tool is connected to said power source and said tool is boring into bone;

wherein the guide wire is extendable into the bone distally beyond the cutting element of the boring tool and up to a desired depth of the channel to be formed by the cutting element.

14. The system as set forth in claim 13 wherein said opening is in the form of an elongated slot extending along said longitudinal axis of said tool.

15. The system as set forth in claim 14 wherein a second elongated slot is located on an opposite side of said wall from said elongated slot.

16. The system as set forth in claim 13 wherein the elongated opening has a first end and a second end, the first end being spaced from a proximal end of the boring tool, and the second end of the opening being located closer to the boring portion than the first end of the opening.

17. The system as set forth in claim 13 wherein the guide wire is a Kirschner wire.

* * * * *